(12) United States Patent
Tull et al.

(10) Patent No.: US 10,787,634 B2
(45) Date of Patent: Sep. 29, 2020

(54) SPACE-EFFICIENT, HIGH THROUGHPUT FERMENTING SYSTEM FOR PRODUCING ALCOHOL-LIMITED KOMBUCHA

(71) Applicant: CLEAR CRAFT, LLC, Waco, TX (US)

(72) Inventors: Toby Tull, Waco, TX (US); David Aycock, Waco, TX (US)

(73) Assignee: CLEAR CRAFT, LLC, Waco, TX (US)

( * ) Notice: Subject to any disclaimer, the term of this patent is extended or adjusted under 35 U.S.C. 154(b) by 0 days.

(21) Appl. No.: 16/796,867

(22) Filed: Feb. 20, 2020

(65) Prior Publication Data

US 2020/0270556 A1    Aug. 27, 2020

Related U.S. Application Data

(60) Provisional application No. 62/809,383, filed on Feb. 22, 2019.

(51) Int. Cl.
   *C12M 1/12*    (2006.01)
   *A23F 3/10*    (2006.01)
   *C12M 1/00*    (2006.01)

(52) U.S. Cl.
   CPC .............. *C12M 23/04* (2013.01); *A23F 3/10* (2013.01); *C12M 23/38* (2013.01); *C12M 29/06* (2013.01)

(58) Field of Classification Search
   CPC ...... C12M 23/04; C12M 23/38; C12M 29/06; A23F 3/10
   See application file for complete search history.

(56) References Cited

U.S. PATENT DOCUMENTS 9,877,494 B2 *    1/2018    Hsu ................... A23F 3/166

FOREIGN PATENT DOCUMENTS

| CA | 2 833 764 | * | 10/2012 |
| CN | 202086162 | * | 12/2011 |

(Continued)

OTHER PUBLICATIONS

Cvetkovic et al., "Specific interfacial area as a key variable in scaling-up Kombucha fermentation", Science Direct, Journal of Food Engineering, 2007.

*Primary Examiner* — Gautam Prakash
(74) *Attorney, Agent, or Firm* — Arc IP Law, PC; Joseph J. Mayo

(57) ABSTRACT

Equipment for fermentation of beverages, particularly kombucha, that limits alcohol production during fermentation, increases throughput by reducing fermentation times, and utilizes production plant floorspace efficiently. Unlike traditional fermentation equipment that uses large, often cylindrical, vats, embodiments of the invention use vertical stacks of relatively shallow fermentation trays. The shallow trays increase the ratio of surface area to liquid volume, thereby improving oxygen flow to the fermenting liquid; increased oxygen flow reduces alcohol production for kombucha and reduces fermentation time. Air gaps between trays in the vertical stack, and headspace between the top of the fermenting liquid and the tray top edges, are optimized to promote oxygen flow. Fermentation trays are stacked vertically to maintain high production capacity with limited facility floorspace. An additional benefit of vertically stacked shallow trays is that heat generated by fermentation flows vertically up the stack, warming the trays without an external heat source.

11 Claims, 13 Drawing Sheets

(56) References Cited

FOREIGN PATENT DOCUMENTS

| | | | |
|---|---|---|---|
| CN | 203524376 | * | 4/2014 |
| CN | 103416545 | * | 1/2015 |
| RU | 2 500 299 | * | 10/2013 |
| WO | WO 98/434489 | * | 10/1998 |

* cited by examiner

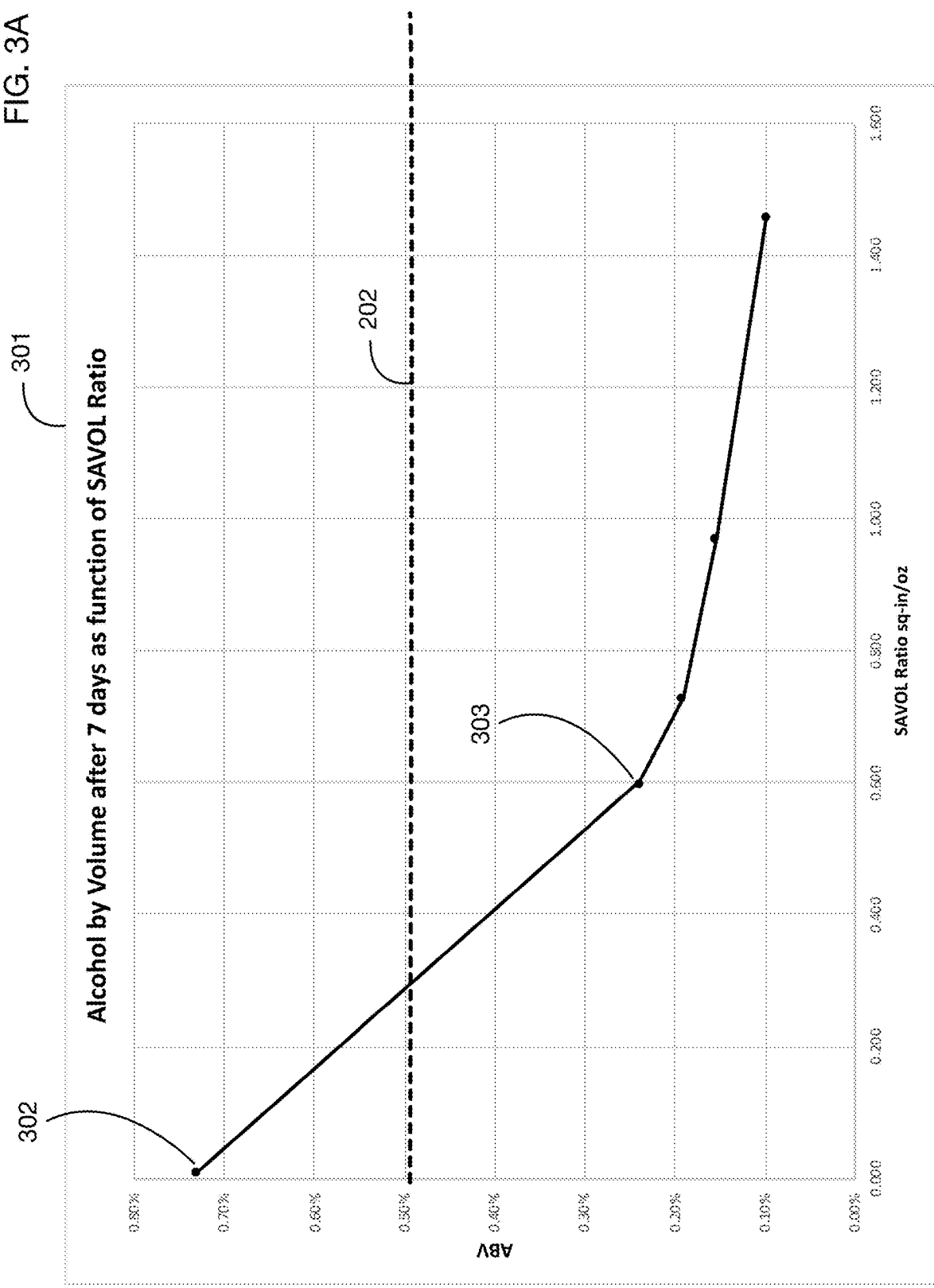

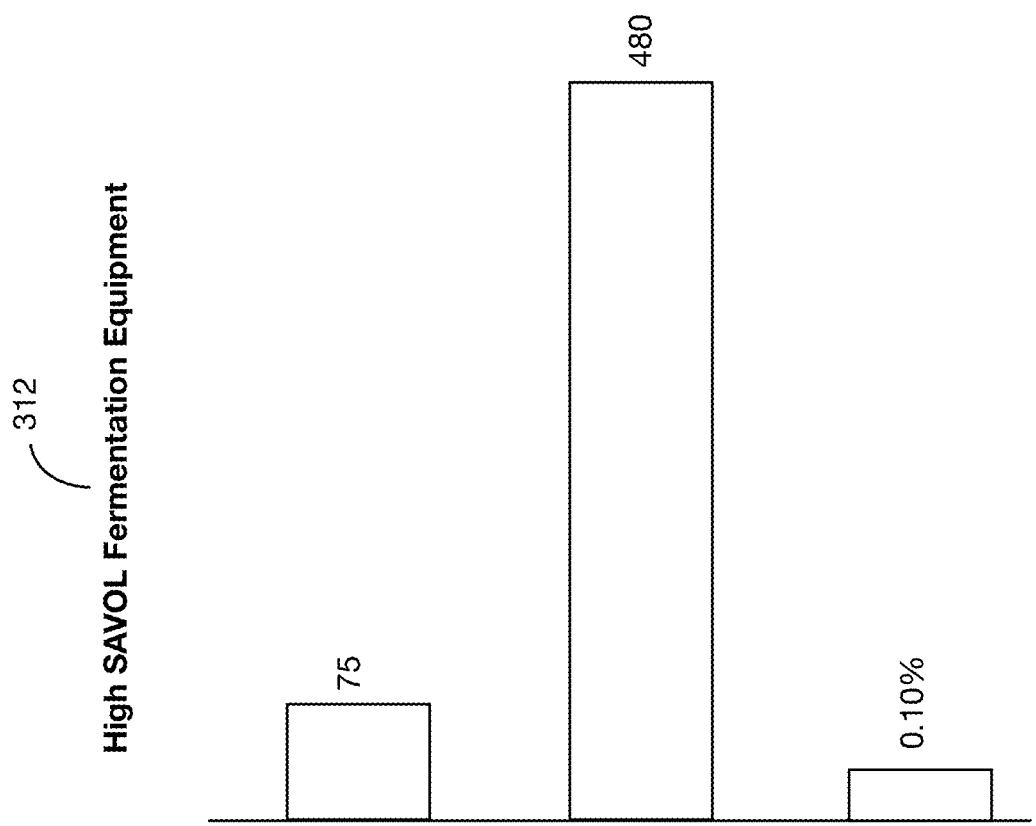
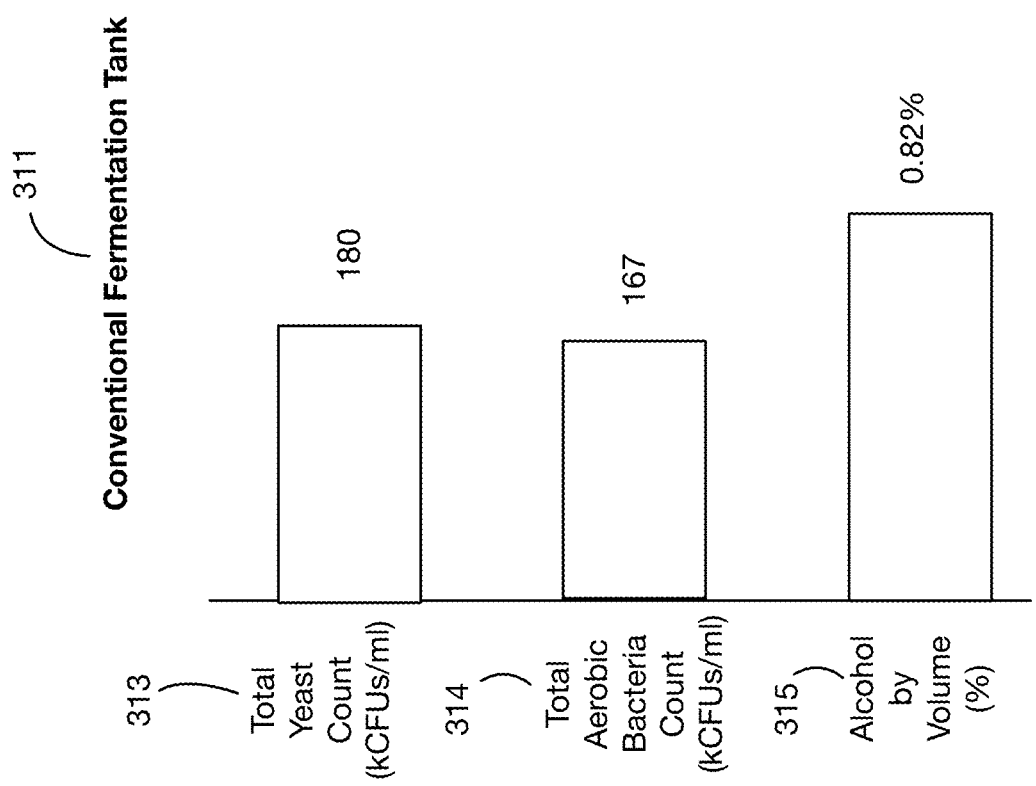
FIG. 3B

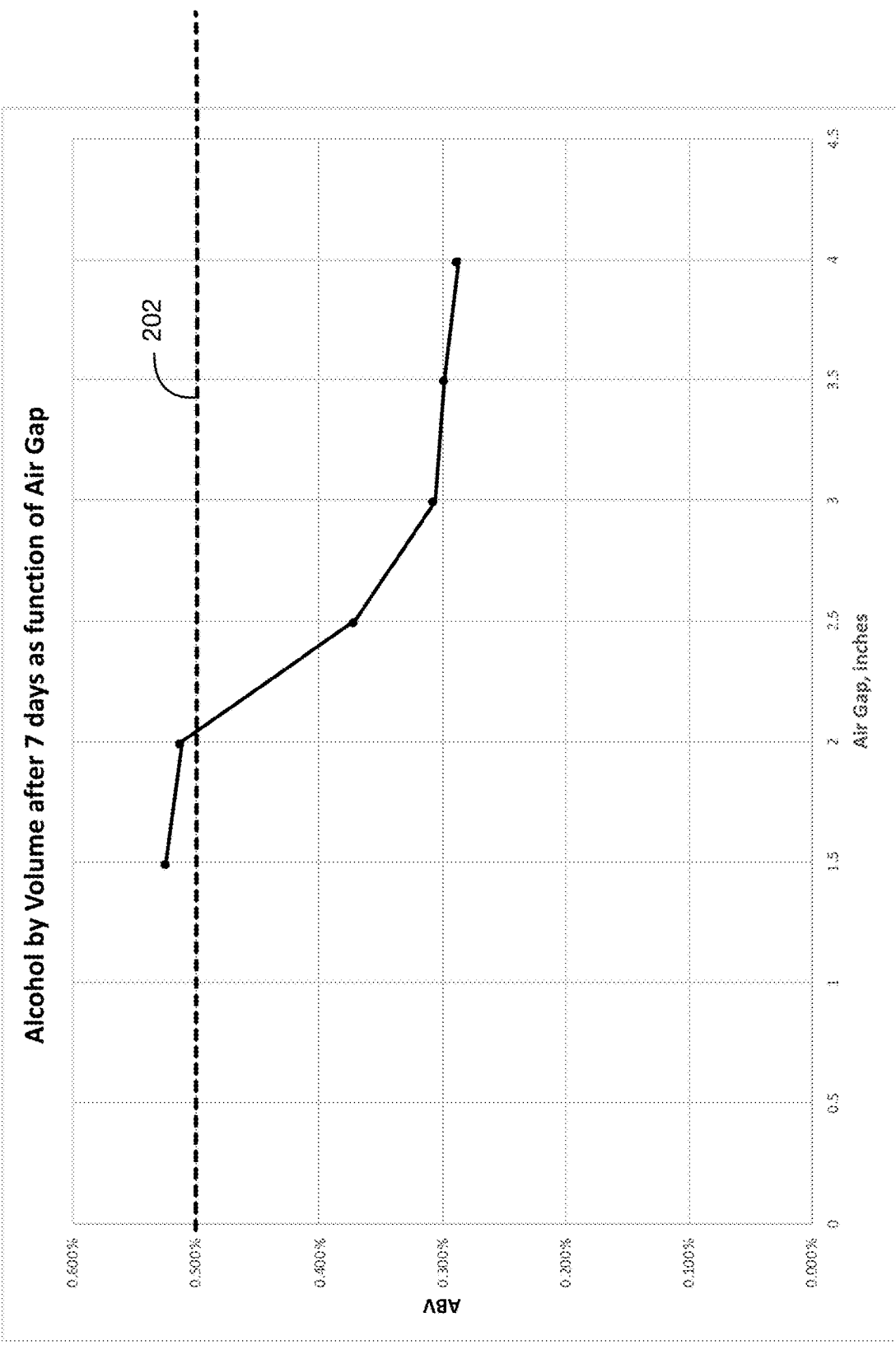

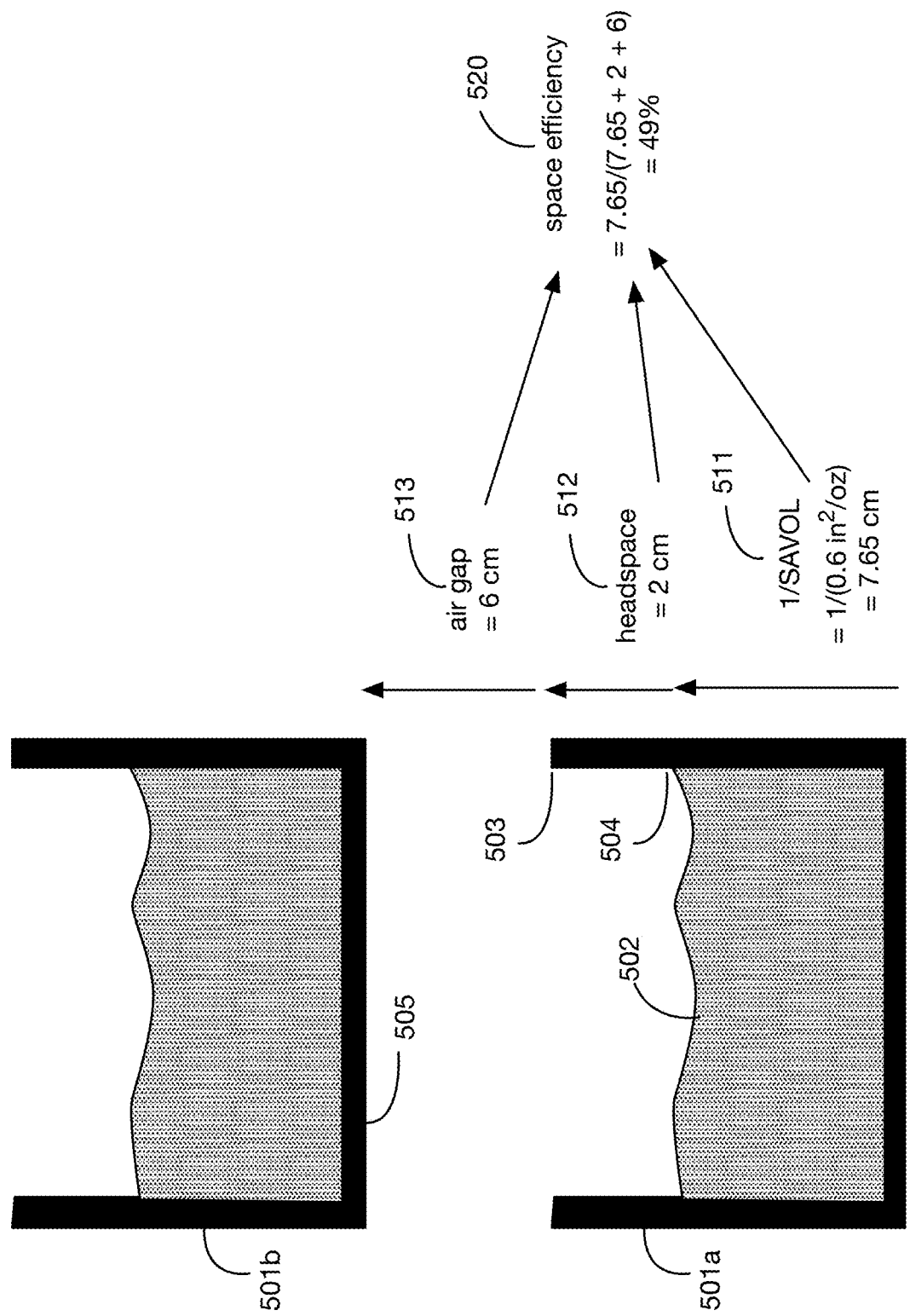

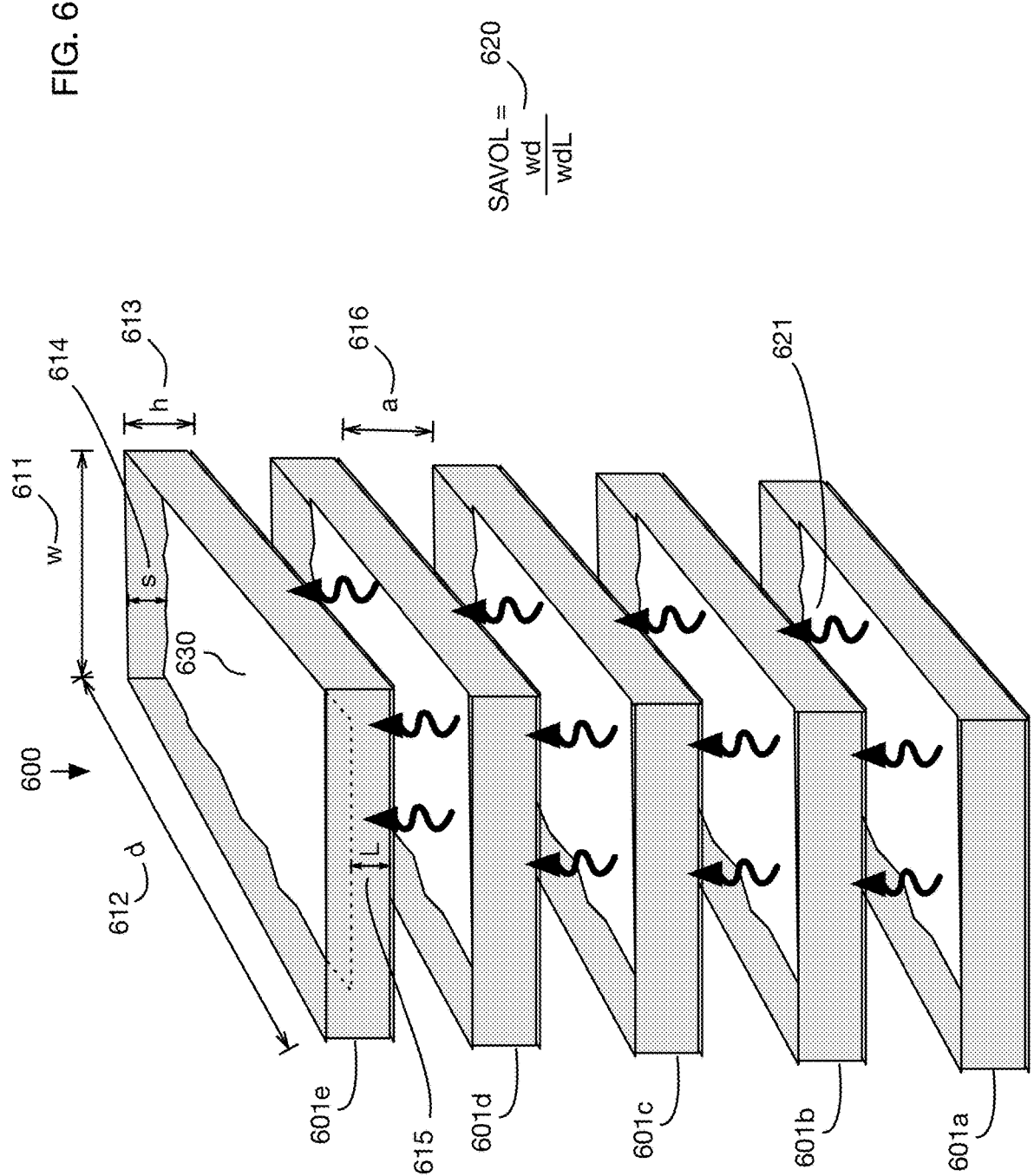

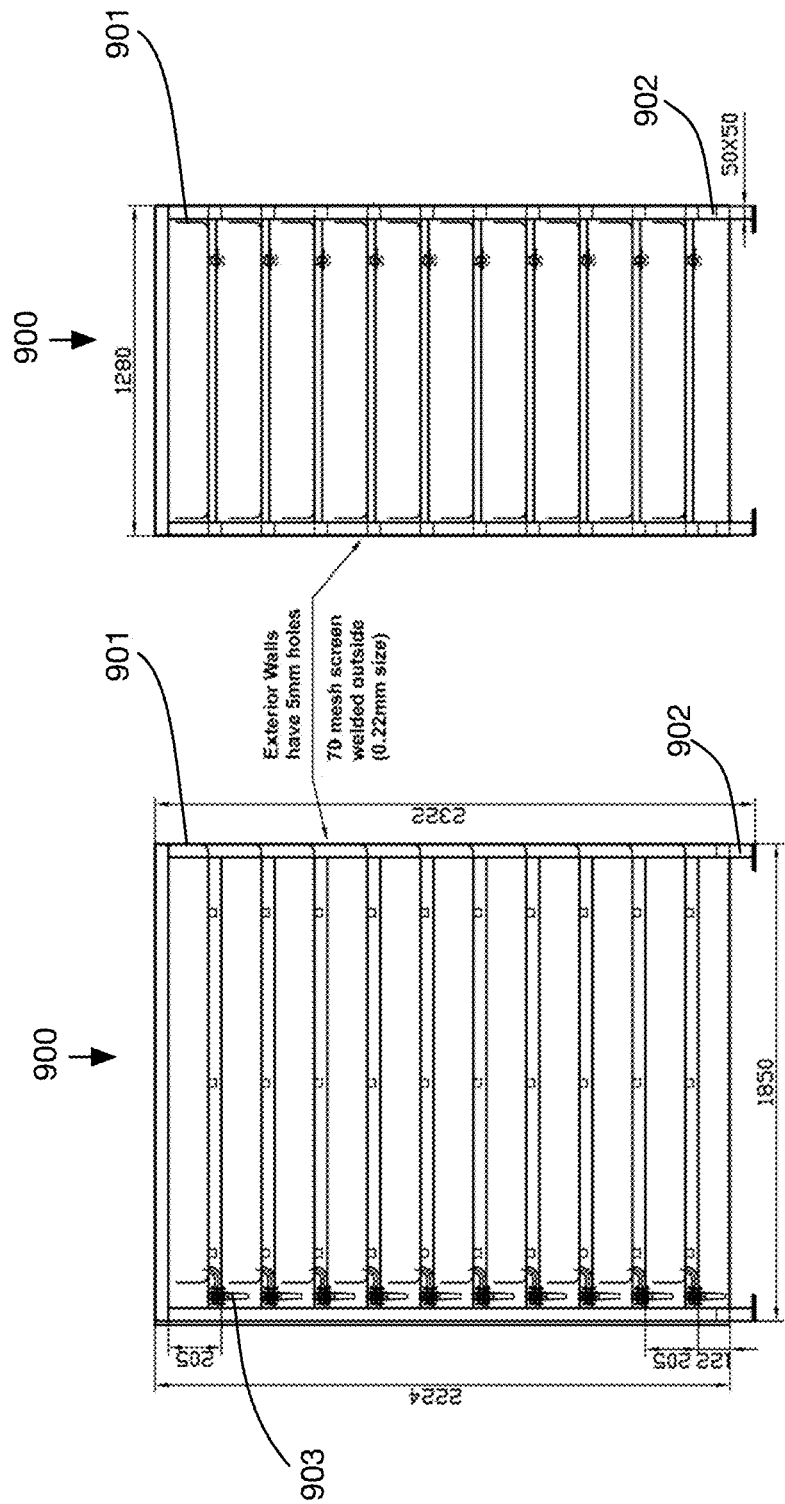

SPACE-EFFICIENT, HIGH THROUGHPUT FERMENTING SYSTEM FOR PRODUCING ALCOHOL-LIMITED KOMBUCHA

This patent application claims the benefit of U.S. Provisional Patent Application Ser. No. 62/809,383, filed 22 Feb. 2019, the specification of which is hereby incorporated herein by reference.

BACKGROUND OF THE INVENTION

Field of the Invention

One or more embodiments of the invention are related to the field of processing and brewing equipment for fermented beverages, such as kombucha. More particularly, but not by way of limitation, one or more embodiments of the invention enable a space-efficient, alcohol-limiting, high throughput fermenting system.

Description of the Related Art

Industrial-scale brewing processes for fermented beverages are typically performed in large vessels. For brewing of kombucha—a fermented beverage made from sweetened tea—the vessels are typically open at the top because fermentation requires oxygen exchange for the yeast and bacteria in the kombucha mixture to ferment the sweetened tea.

For years, a main challenge within the kombucha industry has been to manage the alcohol (ethanol) content of kombucha. By law, manufacturers must keep the liquid below the 0.5% alcohol by volume (ABV) limit set by the TTB (Alcohol and Tobacco Trade Bureau). If the ABV of kombucha rises above 0.5% at any point during the fermentation process, the product is taxable by the TTB as an alcoholic beverage.

When kombucha is fermented in the large open cylindrical vessels that are typically used in existing industrial operations, alcohol content generally exceeds the 0.5% allowable level. To maintain ABV under 0.5%, producers resort to heavy filtration, dilution, pasteurization, and other post-fermentation methods. These steps add cost and time to the production process, and they may adversely affect the quality of the final product.

Another important factor in kombucha brewing is the speed of the fermentation process. Shallower fermentation vessels may allow for more rapid fermentation, due to increased oxygen flow to the mixture. However, existing operations generally use larger vessels, in part to maximize their production capacity per amount of plant floorspace. Some operators attempt to speed up fermentation by heating the mixture, for example with heaters or jackets surrounding the fermentation vessels; this heating also adds expense and complexity to the production process.

For at least the limitations described above there is a need for a space-efficient, alcohol-limiting, high throughput fermenting system.

BRIEF SUMMARY OF THE INVENTION

One or more embodiments of the invention are related to a space-efficient, alcohol-limiting, high throughput fermenting system. Embodiments may be used for example to ferment kombucha or other fermented beverages or mixtures. Potential benefits of the invention include reduced alcohol production and faster fermentation while maintaining the space efficiency of a processing facility.

One or more embodiments of the invention may have a vertical stack of three or more fermenting trays (also referred to in this specification as fermentation trays). Each tray may be used to ferment a liquid such as kombucha. The tops of the trays may be open to the air to allow oxygen flow into the liquid. An air gap may be left between the top edge of one tray and the bottom surface of the tray just above it in the vertical stack. In one or more embodiments, the fermenting trays may be shaped as substantially rectangular parallelepipeds with an open top. The surface area of such a fermenting tray may be substantially equal to the product of the length and width of the tray. The liquid within the tray during fermentation may not be filled to the top. Instead a head space may be left between the top edge of the tray and the top surface of the liquid. The liquid height of the liquid may then be the height of the fermenting tray less the head space. The liquid volume may be approximately equal to the liquid height times the surface area.

In one or more embodiments of the invention, various parameters of the vertical stack and the individual fermenting trays may be configured within certain ranges to improve or optimize the performance of the fermentation process. For example, in one or more embodiments the head space may be between 2 centimeters and 4 centimeters, inclusive; the air gap may be between 5 centimeter and 18 centimeters, inclusive; and the ratio of the surface area to the liquid volume may be greater than or equal to 0.15 square inches per ounce.

In one or more embodiments the fermentation trays may be thermally conductive. For example, the sides and bottom of each fermenting tray may be made of a thermally conductive material such as stainless steel or another metal. The vertical stack of fermentation trays may be configured so that heat flows from one tray to another in the vertical stack. This vertical heat flow may be sufficient so that the fermentation process occurs without an external source of heating.

In one or more embodiments, a drainage spout may be attached to the bottom of each fermenting tray. The bottom surface of the fermenting trays may be sloped so that the drainage spout is at or near the lowest point of the bottom surface.

One or more embodiments may include a mesh cover that attaches over the open top of each fermenting tray; this cover may for example prevent entry of insects into the tray while allow air flow into the tray.

One or more embodiments may include a frame on which the fermenting trays rest. A mesh cover may surround the frame to prevent entry of insects while permitting air flow.

One or more embodiments may have a vertical stack of ten or more fermenting trays.

In one or more embodiments the ratio of surface area to liquid volume may be 0.35 square inches per ounce or greater. In one or more embodiments this ratio may be 0.60 square inches per ounce or greater.

BRIEF DESCRIPTION OF THE DRAWINGS

The above and other aspects, features and advantages of the invention will be more apparent from the following more particular description thereof, presented in conjunction with the following drawings wherein:

FIG. 3A shows results of experiments by the inventors that brewed kombucha using equipment with various ratios of surface area to volume ("SAVOL"), indicating that equipment with higher SAVOL ratios results in lower alcohol production—a significant benefit compared to the prior art.

FIG. 3B shows illustrative contents of finished kombucha brewed using a traditional vessel compared to kombucha brewed using an embodiment of the invention with a high SAVOL ratio; this comparison shows that the embodiment of the invention resulted in kombucha with lower yeast count, higher bacteria count, and lower alcohol content.

FIG. 4 shows results of further experiments by the inventors that brewed kombucha using vertically stacked trays with different air gaps between trays (air gap being the distance between the top edge of one tray and the bottom surface of the tray above it), indicating that higher air gaps further reduce alcohol production.

FIG. 5 illustrates the effect of various equipment configuration parameters on space efficiency of a production plant.

FIG. 6 shows a conceptual diagram of an embodiment of the invention, illustrating some of the important dimensions and ratios for the equipment.

FIG. 8A is a front view of a vertical stack; FIG. 8B is a side view of the vertical stack; FIG. 8C is a top view of an individual fermentation tray; FIG. 8D shows a top view of the tray resting on a frame; FIG. 8E shows a front view of an individual fermentation tray; and FIG. 8F shows a side view of an individual fermentation tray.

FIGS. 9A through 9E show another illustrative embodiment of the invention, which has a vertical stack of 10 fermentation trays. FIG. 9A is a side view of a vertical stack; FIG. 9B is a front view of the vertical stack; FIG. 9C is a top view of an individual fermentation tray; FIG. 9D shows a side view of an individual fermentation tray; and FIG. 9E shows a front view of an individual fermentation tray.

DETAILED DESCRIPTION OF THE INVENTION

A space-efficient, alcohol-limiting, high throughput fermenting system will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

One or more embodiments of the invention enable efficient and effective production of fermented beverages. An illustrative application of the invention is for production of kombucha, a beverage made by fermenting sweetened tea. One or more embodiments may be used for production of any fermented beverages or fermented products, including but not limited to kombucha.

Figure 1:
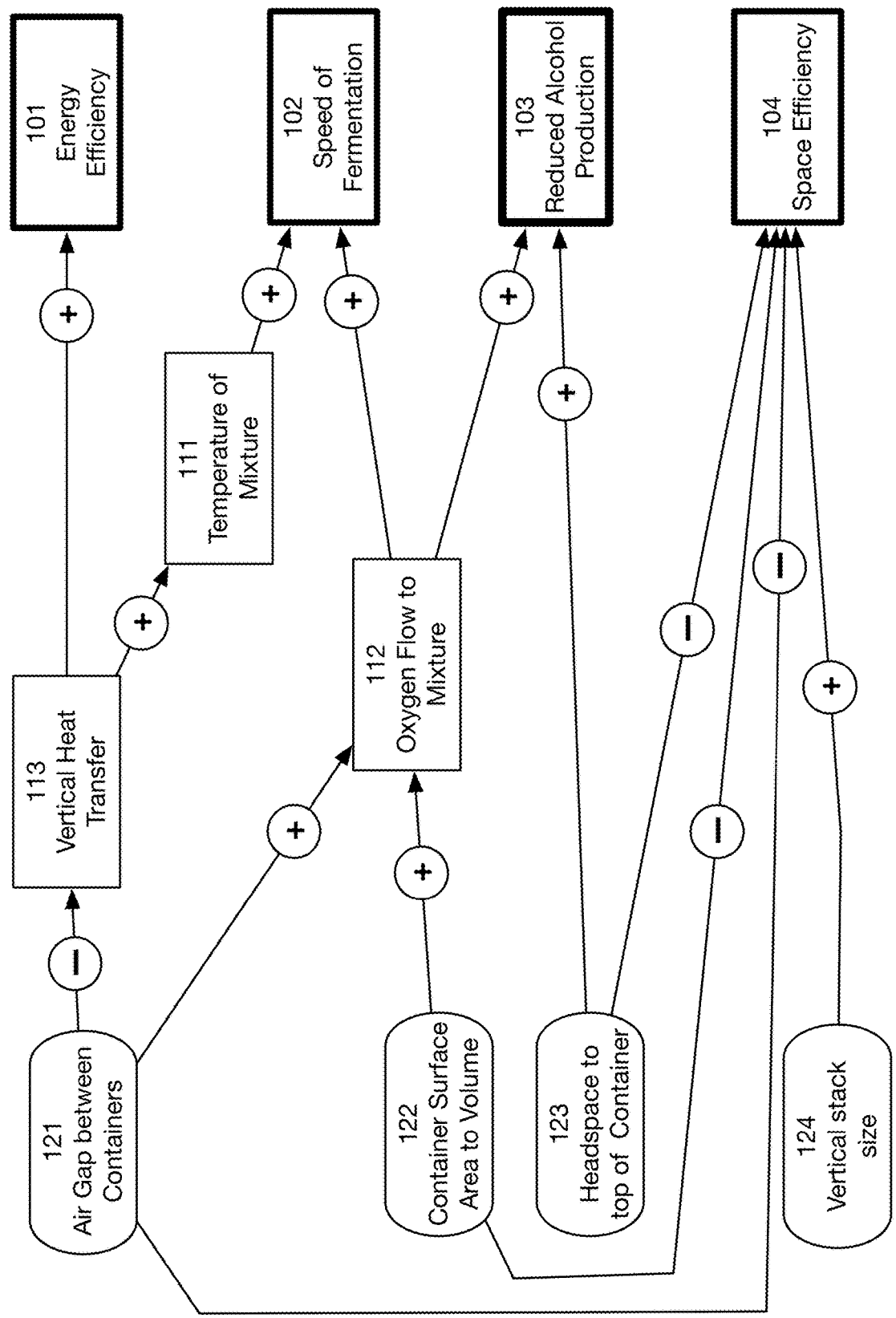
FIG. 1 shows a diagram of key performance parameters in kombucha production, design factors for brewing equipment, and causal links between design factors and performance parameters.

Kombucha production, in particular, is an intricate process that involves several complex tradeoffs and constraints. The inventors have conducted extensive experimentation with various styles and configurations of fermentation equipment to identify equipment characteristics and parameters that optimize these tradeoffs. FIG. 1 shows an overview of key factors identified by the inventors that affect kombucha fermentation performance, and the causal links they have discovered between these factors and the performance characteristics of the process. A positive sign on a causal arrow indicates that a factor at the tail of the arrow has a positive effect on the item at the head of the arrow, and conversely a negative sign indicates a negative effect. Equipment that is configured using these identified parameters is described in subsequent figures.

Typical objectives for kombucha production include maximizing energy efficiency 101 of the process, increasing (within certain limits) the speed of fermentation 102 in order to increase the output of the production facility, reducing alcohol production 103 of the fermentation process so that kombucha is within legal limits without extra processing steps, and maximizing the space efficiency 104 of the plant, for example by producing as much kombucha as possible for a given area of plant floorspace. There may be tradeoffs among some of these factors; as an example, speed of fermentation 102 may be increased by heating the kombucha mixture, but this adversely affects energy efficiency 101.

Production of kombucha involves the fermentation of sweetened tea using a symbiotic culture of bacteria and yeast (also known as a SCOBY). As with all fermentation, the yeast consumes the sugar and produces ethanol and carbon dioxide. The ethanol is then metabolized by the bacteria to create amino acids, enzymes, and acids. Most fermentations are considered "complete" when acetic acid levels reach between 3500 milligrams and 6000 milligrams per liter, though ultimately this determination is made on a manufacturer-by-manufacturer basis based on its desired flavor profile. The speed of fermentation 102, which is a critical driver of plant throughput, is affected by many variables. The inventors have discovered that two variables have the greatest effect on fermentation speed 102: the temperature 111 of the kombucha mixture, and the oxygen flow to the mixture 112. (Oxygen flow may also be referred to as "oxygen mass transfer" in scientific and engineering literature; this term refers to the rate of transfer of oxygen from the air into the liquid.) All kombucha fermentation involves oxygen, which is why kombucha is fermented in open containers. However the rate of oxygen flow into the mixture is a critical variable that affects fermentation speed and, as described below, alcohol production.

During fermentation, the yeast is typically more effective at consuming sugar and producing ethanol than the bacteria is at metabolizing that alcohol. As a result, ethanol levels typically rise during fermentation as the bacteria within the culture struggles to "keep up" in metabolization of alcohol with the yeast's production of alcohol. As described above in the Description of the Related Art, alcohol levels therefore often exceed allowable amounts, requiring post-processing of the kombucha to remove alcohol from the finished product. The inventors have discovered that alcohol production can be limited by increasing the oxygen flow 112 to the mixture, using specially configured equipment as described below, and that by sufficiently increasing this oxygen flow 112 using this equipment it is unnecessary to post-process the kombucha to remove alcohol. This alcohol-limiting feature represents a significant improvement over the prior art, since it avoids the time and expense of post-processing steps to remove alcohol and it ensures that the kombucha mixture is legally below alcohol limits throughout the production process.

As indicated in FIG. 1, the inventors have discovered that the increased oxygen flow 112 that occurs when kombucha is fermented using the equipment of one or more embodiments of the invention also increases the speed of fermentation 102, providing an additional benefit.

The inventors have discovered that a key variable that affects oxygen flow 112 to the kombucha mixture is the ratio of the surface area of the fermentation container to its volume. This container surface-area-to-volume ("SAVOL") ratio 122 is a critical design parameter for containers, which has been overlooked in existing kombucha production facilities known in the art. In the existing art, kombucha is generally fermented in cylindrical containers that are relatively tall, providing large batch sizes and using the floorspace of a facility efficiently by filling a large part of the plant volume with kombucha. However, the SAVOL ratio of these types of containers is typically fairly low, and is far below the optimal levels discovered by the inventors to maximize oxygen flow 112. As illustrated below, one or more embodiments of the invention use relatively shallow fermenting trays for kombucha production; these trays have much larger SAVOL ratios 122, and therefore greatly improve oxygen flow 112 compared to the typical cylindrical vats used in the art.

Experimentation by the inventors has also demonstrated that, unexpectedly, an additional "headspace" factor 123 also affects reduced alcohol production 103. The headspace of a container is the vertical distance between the top of the liquid within the container and the top edge of the container. The inventor's experiments show that greater container headspace reduces alcohol production 103, independent of oxygen flow 112.

Although use of containers with a high SAVOL ratio 122 has a beneficial impact on oxygen flow 112, thereby increasing fermentation speed 102 and reducing alcohol production 103, these containers are less space-efficient than tall vessels that fill a large fraction of the space of a production plant. To compensate for this negative effect of SAVOL ratio 122 on space efficiency 104, the inventors have discovered that high SAVOL ratio trays may be stacked vertically, thereby making better use of plant floorspace. The number of trays in a vertical stack 124 is directly related to the space efficiency 104 in the plant, since more trays per stack increases the output of the plant per unit of floorspace. (Trays can only be stacked up to a practical limit based on the ceiling height of the plant or other physical or operational constraints.)

However, vertical stacking of trays 124 to increase space efficiency 104 introduces another complex tradeoff in the production process, since tightly stacked trays may impede air flow to the surface of the liquid in the trays, thereby impeding oxygen flow 112. To ensure sufficient oxygen flow 112, the inventors have experimented with various configurations that leave an air gap 121 between the containers (specifically a gap between the top edge of one container and the bottom surface of the next highest container in the vertical stack). A larger air gap 121 improves oxygen flow 112, thereby resulting in a higher speed of fermentation 102 and reduced alcohol production 103. However, larger air gaps 121 have a negative effect on space efficiency 104, since trays are more spread out in the vertical stack.

Unexpectedly, the inventors have discovered that another benefit of vertically stacking trays is that the heat generated during fermentation may flow from one tray to the tray above. This vertical heat transfer 113 may reduce or eliminate the need for external heat sources to drive fermentation, thereby improving energy efficiency 101 of the plant. However, larger air gaps 121 between trays may at some point have a negative effect on this vertical heat transfer 113; thus finding an optimal air gap 121 is a complex process that trades off effects on vertical heat transfer 113, oxygen flow 112, and space efficiency 104.

Figure 2:
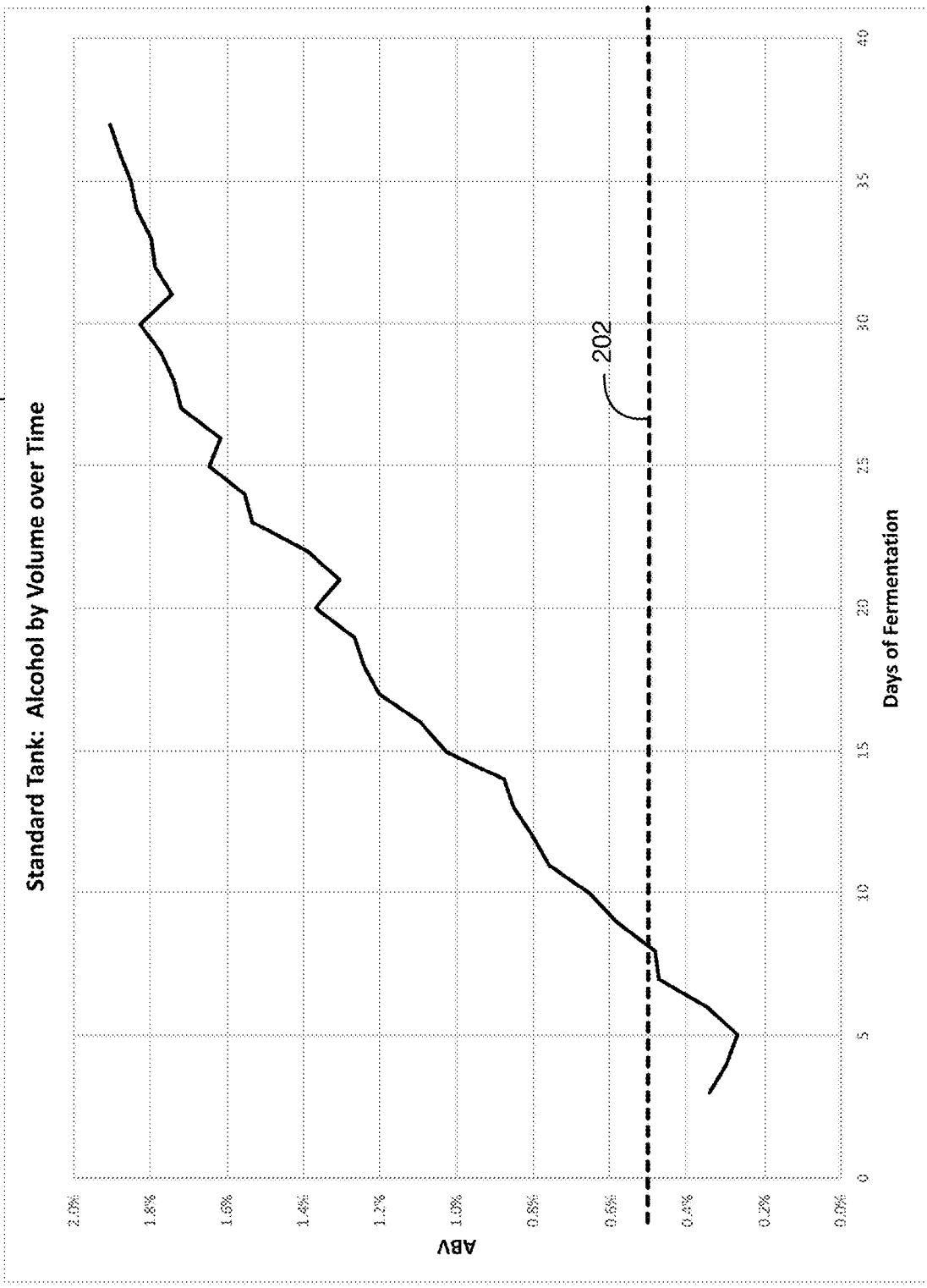
FIG. 2 shows illustrative alcohol production during kombucha production using equipment available in the prior art; alcohol quickly exceeds the legal limit of 0.5% ABV.

Focusing first on the alcohol production performance parameter 103, FIG. 2 shows typical performance of fermentation equipment available in the prior art. The graph 201 shows alcohol by volume of a kombucha mixture as a function of the elapsed number of days of the fermentation process. This experiment was performed in a cylindrical 200-gallon fermentation tank (38 inches diameter, 41 inches from the floor to the rim, and a SAVOL of 0.04662), which is typical of the equipment currently used for kombucha production. After approximately 7 days, alcohol by volume exceeds the legal limit 202 of 0.5%. As described above, this excessive alcohol production generally necessitates post-processing to remove alcohol from the finished product.

FIG. 3A shows the results of kombucha brewing experiments by the inventors using equipment of different SAVOL ratios. The SAVOL ratio is defined as the ratio of the surface area of the kombucha mixture divided by its volume. In graph 301 of FIG. 3A, the SAVOL ratio is measured in units of square inches per fluid ounce. The graph shows the alcohol by volume of the kombucha mixture after 7 days of fermentation with different equipment. Point 302 shows results of fermentation using a typical brewing vat similar to that used in the experiment of FIG. 2, with a SAVOL ratio of 0.011. Alcohol after 7 days exceeds the legal limit 202 of 0.5%. As the SAVOL ratio of equipment is increased, alcohol by volume is reduced. For example, point 303 shows the results of fermenting with equipment having a SAVOL ratio of 0.6; alcohol level is far below the legal limit 202.

Increased SAVOL ratios reduce alcohol content because the higher oxygen delivered into the kombucha mixture increases the amount and effectiveness of the aerobic bacteria in the mixture. The bacteria can then keep up with the yeast's production of ethanol. In addition to reducing alcohol, a higher SAVOL ratio changes the amount of residual bacteria and yeast in the finished kombucha product. This effect is illustrated in FIG. 3B, which shows results of experiments by the inventors comparing the kombucha generated using a traditional fermentation tank 311 to that generated using an embodiment of the invention 312 with a substantially higher SAVOL ratio. The yeast counts 313 are significantly higher using the traditional tank 311, and the bacteria counts are significantly higher using the embodiment of the invention 312. As expected, this change in the balance between bacteria and yeast results in much lower alcohol 315 for the embodiment of the invention 312. In addition to lower alcohol, the higher bacteria count and lower yeast count resulting from the embodiment of the invention improves the quality of the kombucha product, since the bacteria in kombucha generally provides health benefits while excessive yeast can be detrimental.

As discussed above with respect to FIG. 1, the inventors have discovered that for vertical stacks of fermentation trays, the air gap between the trays also has a significant effect on oxygen flow, and hence on alcohol production. FIG. 4 shows the results of experiments by the inventors using a vertical stack of fermenting trays with different air gaps between the trays. Graph 401 of alcohol by volume after 7 days of fermentation as a function of air gap indicates that higher air gaps reduce the production of alcohol.

Turning now to the issue of space efficiency 104, FIG. 5 illustrates some of the tradeoffs between space efficiency and other factors. For simplicity, FIG. 5 shows an illustrative vertical stack of two fermentation trays, 501*a* and 501*b*. (One or more embodiments may have any number of fermentation trays in a vertical stack, depending in part on the desired plant capacity and on the vertical height of the processing plant). In fermentation tray 501*a*, kombucha mixture 502 is not filled to the top of the tray; instead headspace 512 is left between the top edge 503 of the tray and the top 504 of the liquid mixture 502. An air gap 513 separates the top edge 503 of tray 501*a* and the bottom surface 505 of the tray 501*b* above it in the vertical stack. The height 511 of the liquid 502 in tray 501*a* is related to the SAVOL ratio of the fermentation tray. This height 511 is effectively the inverse of the SAVOL ratio for a container that is roughly shaped as a rectangular parallelepiped, since SAVOL is area divided by volume, and volume is area times the height 511 of the liquid. From the figure it is apparent that a greater air gap and greater head space reduce the amount of vertical space devoted to the kombucha mixture, thereby reducing space efficiency; however, larger air gaps and headspace improve performance of the process by reducing alcohol production, reducing fermentation time, and improving vertical heat flow, as described with respect to FIG. 1. Optimal selection of air gaps and headspace therefore represents an engineering challenge that must consider all of the factors of kombucha production. For the illustrative parameter values shown in FIG. 5, the resulting space efficiency 520 is 49%. These parameter values are shown only for illustration of the tradeoffs.

FIG. 6 shows a conceptual diagram of an embodiment 600 of the invention that incorporates factors identified in FIG. 1 to optimize the tradeoffs in kombucha production. In this illustrative embodiment, the vertical stack of fermentation trays includes 5 trays: 601*a*, 601*b*, 601*c*, 601*d*, and 601*e*. These trays are roughly shaped as rectangular parallelepipeds with open tops. In one or more embodiments the fermentation trays may have any desired shapes; a potential benefit of rectangular trays is that they may be packed closely together to maximize space efficiency. Although the trays are substantially rectangular, they may have slight slopes or other features; for example the bottom surfaces of the trays may be angled towards a drainage spout to facilitate emptying of the trays. The trays may be rest on one or more frames; for simplicity these frames are not shown in FIG. 6.

Dimensions of several configuration parameters are illustrated for the top tray in the stack 601*e*. This tray has a depth 612, a width 611, and a height 613. During the fermentation process, the tray is filled with kombucha mixture 630 to a liquid height of 615 from the bottom surface of the tray to the top surface of the liquid. In one or more embodiments this liquid height 615 may be less than the total height 613 of the tray (from its bottom surface to its top edge). The difference between the tray height 613 and the liquid height 615 is the headspace 614. The SAVOL ratio of the fermenting tray 630 is the ratio of the surface area of the top surface of the liquid 630 to the volume of liquid contained in the tray. For a rectangular tray as illustrated in FIG. 6, this ratio is equal to the width 611 times the depth 612 divided by the product of width 611, depth 612, and liquid height 615; this is equivalent to the inverse of the liquid height 615. An air gap 616 exists between the top edge of each tray (except for the very top tray) and the bottom surface of the next tray just above it in the vertical stack.

The inventors have experimented extensively with different configurations and parameters and have identified parameter ranges that may be used in one or more embodiments for high performance fermentation operations that optimize tradeoffs among the various factors shown in FIG. 1. For example, in one or more embodiments the air gap 616 may range between 5 centimeters and 18 centimeters, inclusive; the head space may range between 2 centimeters and 4 centimeters, inclusive, and the SAVOL ratio may be 0.15 square inches per ounce or greater. Higher SAVOL ratios may be desirable in one or more embodiments to further reduce alcohol production and to increase fermentation speed, as described and illustrated above; for example, in one or more embodiments the SAVOL ratio of the trays may be 0.35 square inches per ounce or greater, or in some embodiments 0.60 square inches per ounce or greater. One or more embodiments may use any number of trays in the vertical stack, for example the embodiments illustrated below use 4 or 10 trays in the vertical stack.

The vertical stacking of fermentation trays allows vertical heat flow 621 from one tray to the tray above it. Fermentation is an exothermic process, which means that the process of fermentation creates heat. Because heat flows from the lower trays up the vertical stack, one or more embodiments may enable kombucha fermentation without any external heat source. Experiments by the inventors show that vertical heat flow using the parameters specified above for dimensions results in a temperature increase of approximately 1 to 1.5 degrees Fahrenheit for each tray due to heat flow from the tray below, without any external heating. This effect is cumulative, so that the top tray in a vertical stack receives heat flow from all trays below it. The inventors have found that using this configuration kombucha can be fermented effectively without external heating in an ambient temperature of approximately 75 to 78 degrees Fahrenheit. This use of vertical heat flow represents a significant advance over the prior art, which often relies on external heating or on heated jackets surrounding fermentation tanks. For optimal vertical heat flow, one or more embodiments may use fermentation trays constructed of thermally conductive materials, such as stainless steel or other metals for example. In an illustrative embodiment of the invention, the fermentation trays are constructed of stainless steel that is approximately 1.5 millimeters thick.

FIGS. 7 and 8A through 8F illustrate an embodiment of the invention with 4 vertically stacked trays having SAVOL ratios of approximately 0.20 inches squared per ounce, and FIGS. 9A through 9E illustrate an embodiment of the invention with 10 vertically stacked trays having SAVOL ratios of approximately 0.37 inches squared per ounce.

Figure 7:
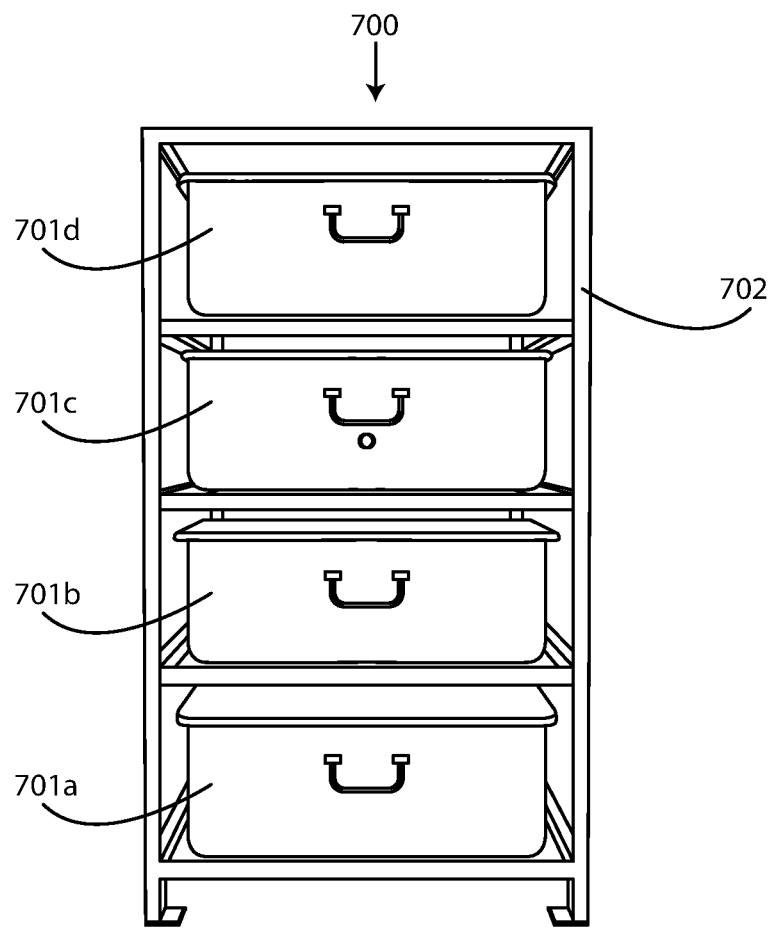
FIG. 7 shows a photograph of an embodiment of the invention with four vertically stacked brewing trays.

FIG. 7 shows a photograph of an embodiment 700 of the invention with four vertically stacked fermentation trays 701*a*, 701*b*, 701*c*, and 701*d*. The trays are rest on a frame 702. Embodiment 700 is a modular design, meaning that additional racks and trays can be added atop one another. A facility may use only one rack, which holds four (4) pans, or it may use two racks and stack them on top of one another, effectively giving them eight trays stacked vertically. Each of the fermentation trays has a lip at the top edge. This lip allows for a brewer to place a breathable mesh covering (such as a cloth or similar material) over each pan and then secure it with a rubber band or elastic, which holds the mesh to each pan below the lip. The coverings may prevent gnats, flies, or other contaminants from entering the kombucha mixture while allowing for air to freely flow through the unit—a crucial aspect with the open fermentation of kombucha.

Figure 8B:
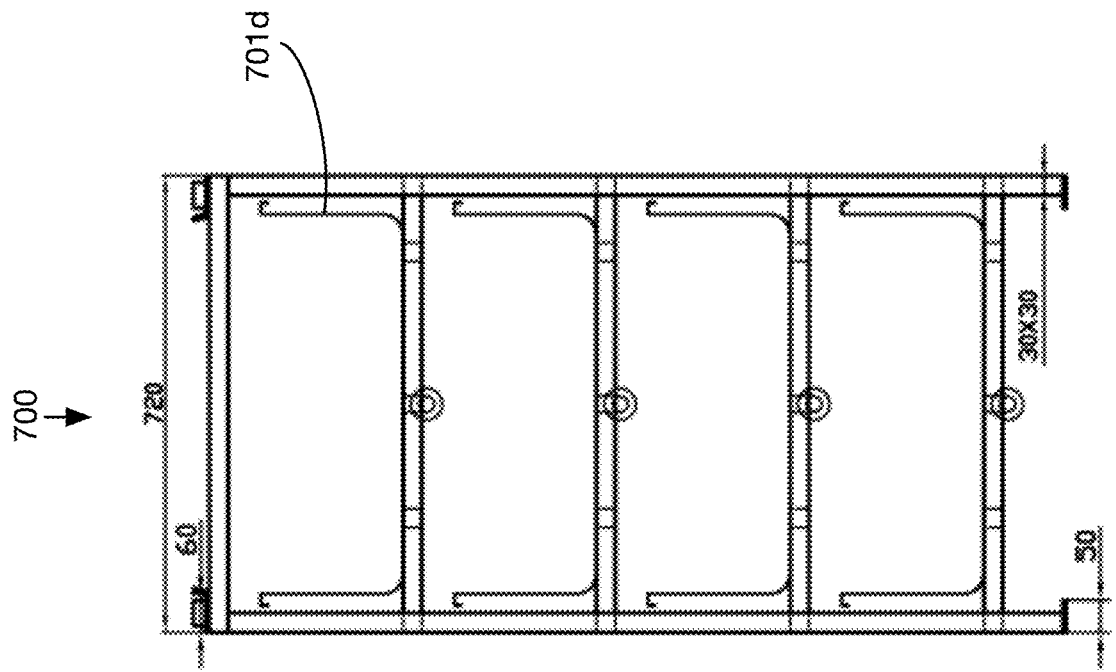
FIGS. 8A through 8F show dimension of the equipment shown in FIG. 7.
Figure 8A:
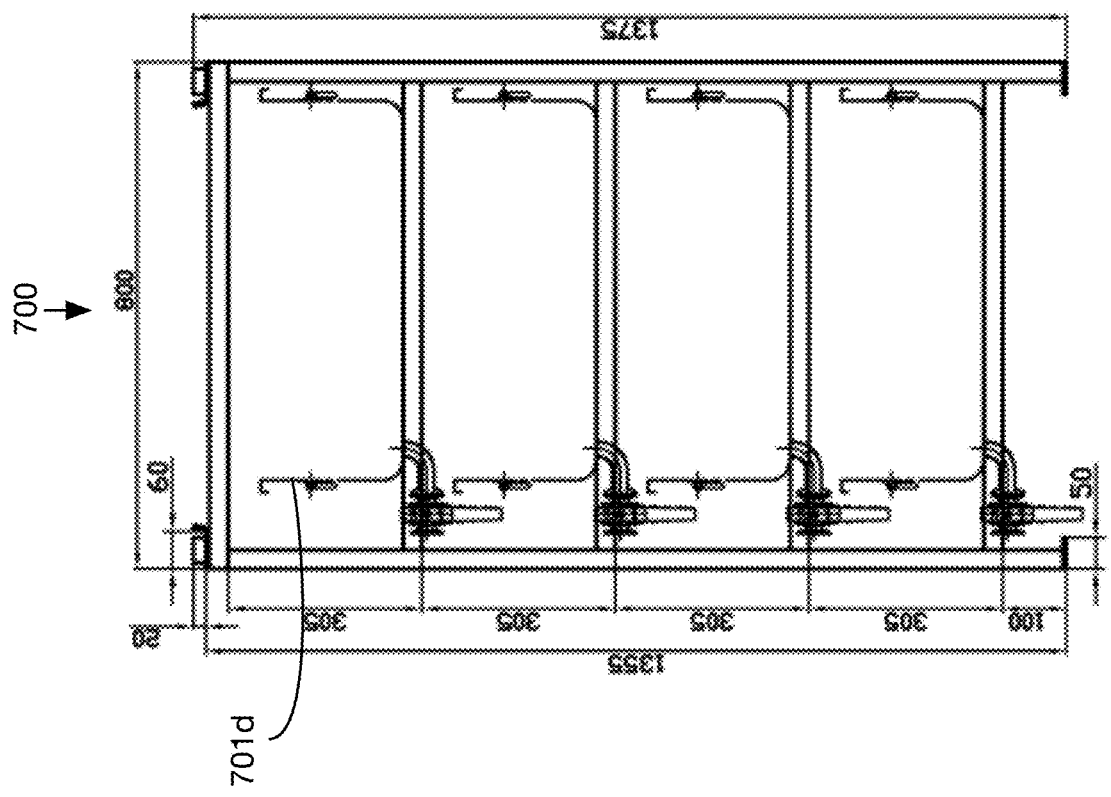
Figure 8D:
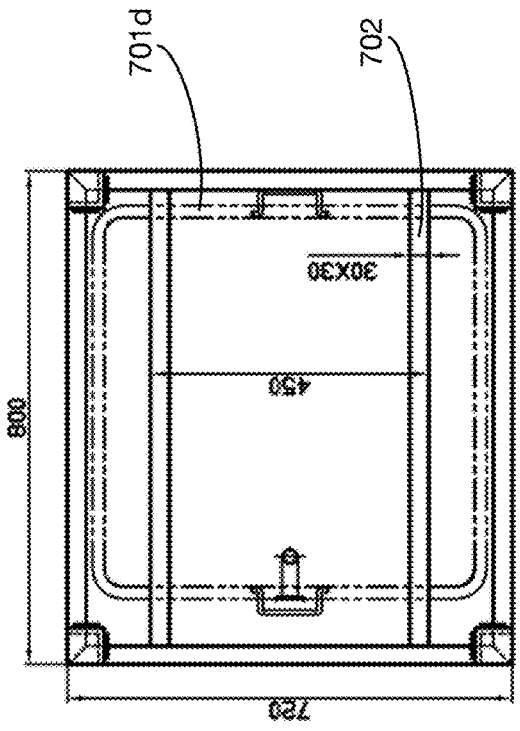
Figure 8C:
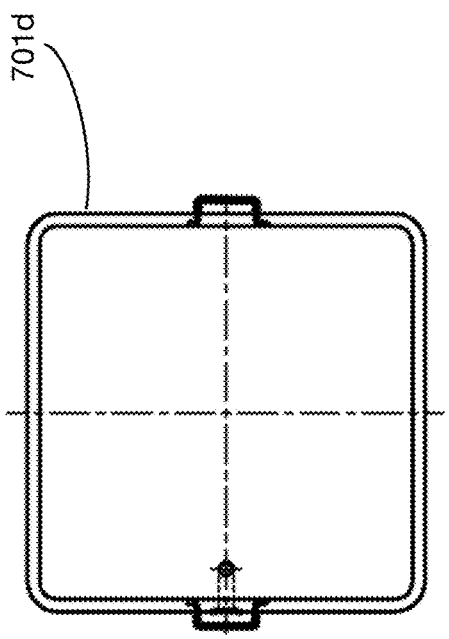
Figure 8F:
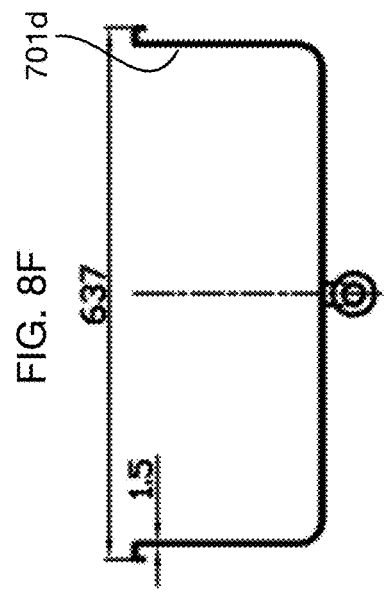
Figure 8E:
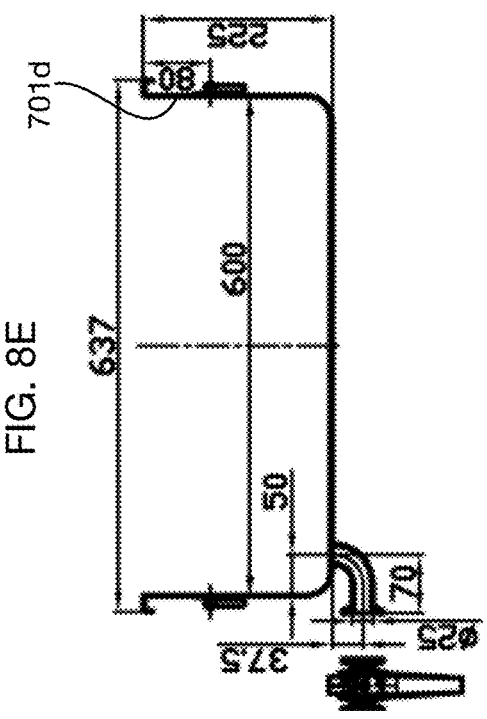

FIGS. 8A and 8B show front and side views, respectively, of the embodiment 700. Dimensions shown on the figures are in millimeters. These dimensions are illustrative; one or more embodiments may use vertical stacks of fermentation trays with any desired dimensions and spacing. The individual fermentation trays of this embodiment, such as top tray 701d, each measure 600 mm wide by 600 mm long by 225 mm high. After converting the surface area to inches-squared and volume to fluid ounces, the resulting SAVOL Ratio for each tray is 0.2037 inches squared per ounce. FIG. 8C shows a top view of an individual fermentation tray 701d of the embodiment 700, and FIG. 8D shows this fermentation tray resting on the frame 702. FIGS. 8E and 8F show front and side views, respectively, of the individual fermentation tray 701d. For this illustrative embodiment 700, the air gap between trays is 3 inches, and the headspace of each tray is 2.5 inches.

Figure 9C:
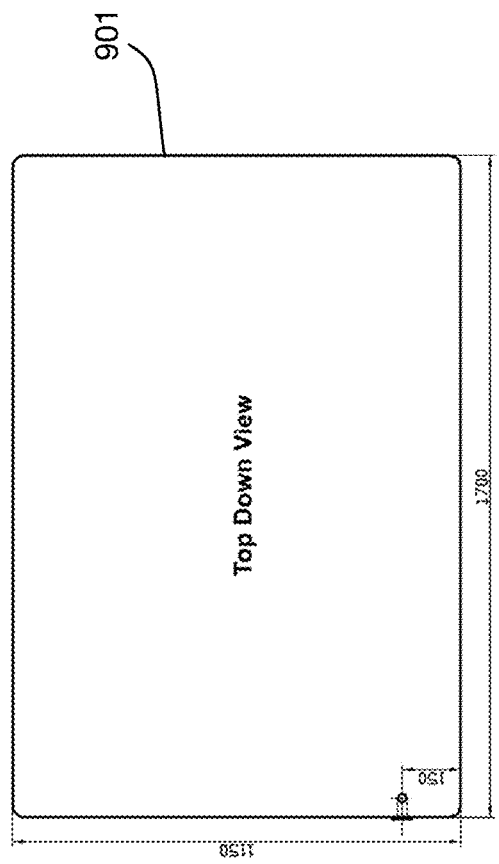

FIGS. 9A through 9E show another illustrative embodiment of the invention. This embodiment 900 has a vertical stack of 10 fermentation trays that are shallower than those illustrated in FIG. 7. FIGS. 9A and 9B show side and front views, respectively, of the vertical stack 900. The 10 stackable stainless steel fermentation trays are suspended, one above another vertically, on a steel frame 902 that may be bolted to the floor if desired. While this particular design incorporates stainless steel vessels with a stainless steel design, it could also utilize vessels made of other materials like glass, plastic, or ceramic. Each tray is equipped with a spout attached to the bottom of the tray which allows an operator to fill and drain liquid via a hose. For example, top fermentation tray 901 has spout 903 on its bottom surface. The entire frame 902 may enclosed in a wire mesh screen to keep out bugs and foreign contaminants. The frame also may have a door that can be opened and closed to work on the trays. When closed, the entire unit is constructed such that it is impermeable to gnats, flies, or other contaminants. However, the fine wire mesh allows for air to freely flow through the unit—a crucial aspect with the open fermentation of kombucha.

Figure 9E:
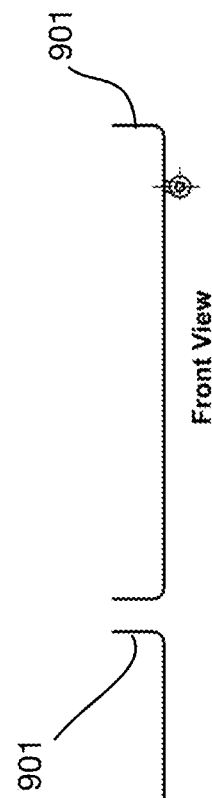
Figure 9D:
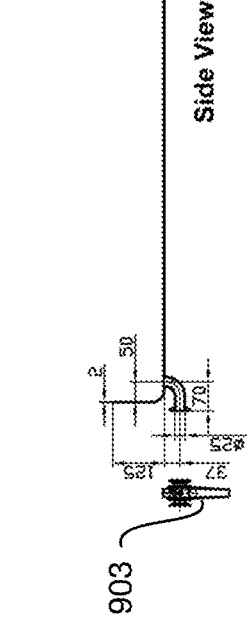

FIGS. 9C, 9D, and 9E show top, side, and front views, respectively, of an individual fermentation tray 901 of vertical stack 900. Each tray measures 1150 mm wide by 1700 mm deep by 125 mm high. After converting the surface area to inches-squared and volume to fluid ounces, the resulting SAVOL Ratio for each tray is 0.3668 in/oz$^{-1}$.

Figure 10:
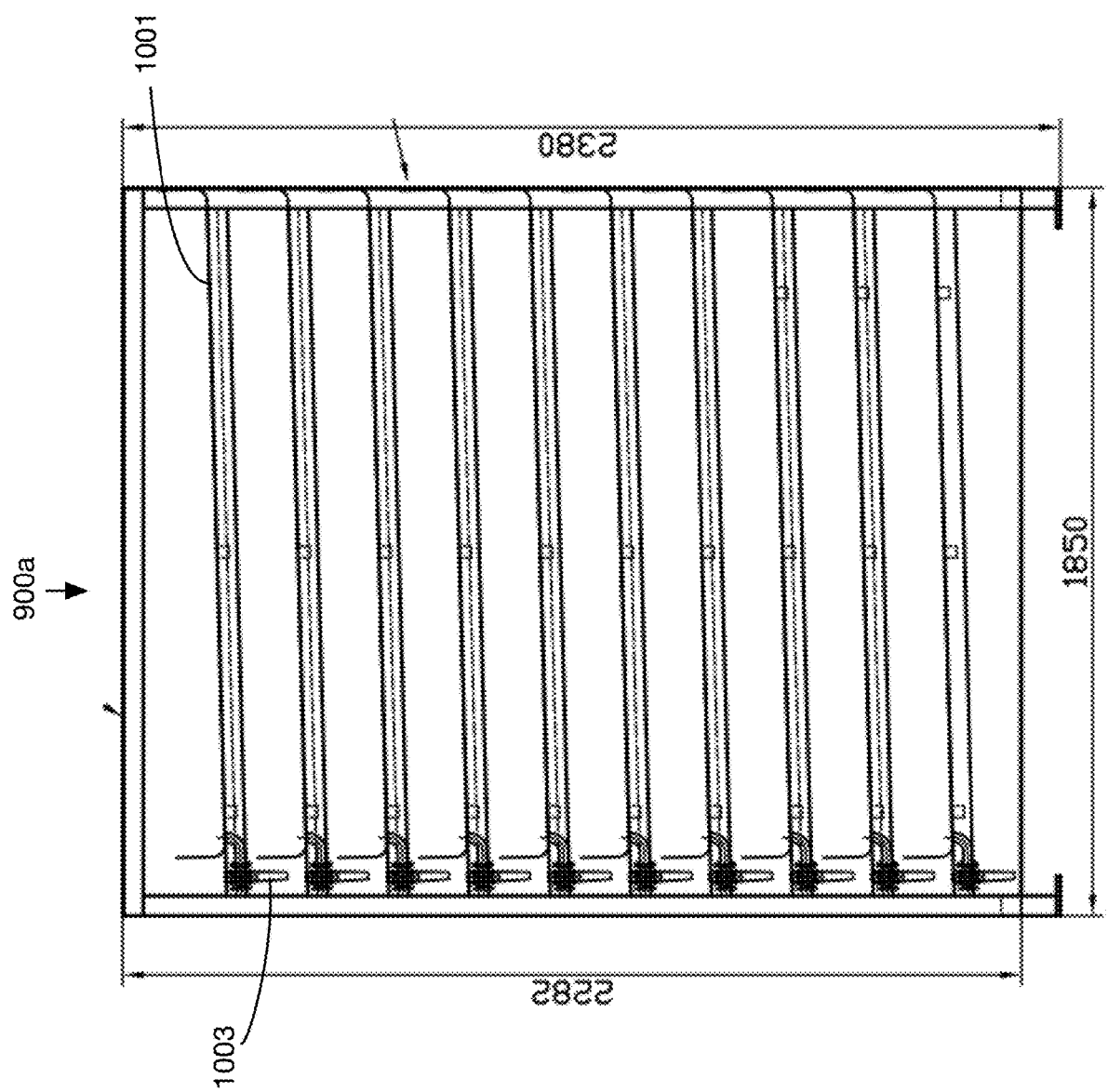
FIG. 10 shows a variation of the embodiment of FIG. 9A with sloped tray bottoms to improve drainage from the fermentation trays.

FIG. 10 shows a side view of a variation 900a of the embodiment of FIG. 9A with sloped tray bottoms. For example, the bottom 1001 of the top fermentation tray in the vertical stack slopes downward towards drainage spout 1003, so that the drainage spout is at or near the lowest point of the bottom surface. These sloped tray bottoms may facilitate emptying of the fermentation trays when fermentation is complete, and may also facilitate cleaning of the trays between fermentation cycles.

While the invention herein disclosed has been described by means of specific embodiments and applications thereof, numerous modifications and variations could be made thereto by those skilled in the art without departing from the scope of the invention set forth in the claims.

What is claimed is:

1. A space-efficient, high throughput fermenting system for producing alcohol-limited kombucha comprising:
  a vertical stack of three or more fermenting trays, wherein each fermenting tray of said three or more fermenting trays is configured to retain a fermentable liquid comprising a sweetened tea and a symbiotic culture of bacteria and yeast during a fermentation process;
  said each fermenting tray comprises an open top wherein a top surface of said fermentable liquid is exposed to air;
  said each fermenting tray further comprises a substantially rectangular parallelepiped with said open top, said parallelepiped comprising
    a length;
    a width;
    a height;
  said each fermenting tray is configured to provide
    a liquid height comprising said height less a head space, wherein said head space comprises a distance between said top surface of said fermentable liquid and a top of said each fermenting tray;
    a surface area comprising a product of said length and said width;
    a liquid volume comprising a product of said surface area and said liquid height;
  said head space is greater than or equal to 2 cm and less than or equal to 4 cm;
  a ratio of said surface area to said liquid volume is greater than or equal to 0.15 square inches per ounce;
  said each fermenting tray except for a top fermenting tray in said vertical stack further comprises an air gap comprising a distance between said top of said each fermenting tray and a bottom of an adjacent tray just above said each fermenting tray in said vertical stack;
  said air gap of said each fermenting tray except for said top fermenting tray is greater than or equal to 5 cm and less than or equal to 18 cm; and
  said each fermenting tray is thermally conductive and is further configured to provide heat to another fermenting tray in said vertical stack.

2. The system of claim 1, wherein said vertical stack of said three or more fermenting trays is configured to provide said heat such that said fermentation process occurs without an external source of heating of said three or more fermenting trays.

3. The system of claim 1, wherein said each fermenting tray further comprises metallic sides and a metallic bottom.

4. The system of claim 1, wherein said each fermenting tray further comprises a drainage spout coupled to the bottom of said each fermenting tray.

5. The system of claim 4, wherein said bottom of said each fermenting tray is sloped such that an opening of said drainage spout is at or proximal to a lowest point in said bottom.

6. The system of claim 1, further comprising a mesh cover attached to said open top of said each fermenting tray, said mesh cover configured to prevent entry of insects into said each fermenting tray and to allow flow of air into said each fermenting tray.

7. The system of claim 1, further comprising
  a frame onto which said each fermenting tray rests; and,
  a mesh cover surrounding said frame, said mesh cover configured to prevent entry of insects into said each fermenting tray and to allow flow of air into said each fermenting tray.

8. The system of claim 1, wherein said vertical stack comprises ten or more fermenting trays.

9. The system of claim 1, wherein said ratio of said surface area to said liquid volume is greater than 0.35 square inches per ounce.

10. The system of claim 1, wherein said ratio of said surface area to said liquid volume is greater than 0.60 square inches per ounce.

11. A space-efficient, high throughput fermenting system for producing alcohol-limited kombucha comprising:
   a vertical stack of ten or more fermenting trays;
      a frame onto which each fermenting tray of said ten or more fermenting trays rests;
      a mesh cover surrounding said frame, said mesh cover configured to prevent entry of insects into said each fermenting tray and to allow flow of air into said each fermenting tray;
      wherein
         each fermenting tray of said ten or more fermenting trays is configured to retain a fermentable liquid comprising a sweetened tea and a symbiotic culture of bacteria and yeast during a fermentation process;
         said each fermenting tray comprises an open top wherein a top surface of said fermentable liquid is exposed to air;
         said each fermenting tray further comprises a substantially rectangular parallelepiped with said open top, said parallelepiped comprising
            a length;
            a width;
            a height;
         said each fermenting tray is configured to provide
            a liquid height comprising said height less a head space, wherein said head space comprises a distance between said top surface of said fermentable liquid and a top of said each fermenting tray;
            a surface area comprising a product of said length and said width;
            a liquid volume comprising a product of said surface area and said liquid height;
         said each fermenting tray further comprises metallic sides and a metallic bottom;
         said head space is greater than or equal to 2 cm and less than or equal to 4 cm;
         a ratio of said surface area to said liquid volume is greater than or equal to 0.35 square inches per ounce;
         said each fermenting tray except for a top fermenting tray in said vertical stack further comprises an air gap comprising a distance between said top of said each fermenting tray and a bottom of an adjacent tray just above said each fermenting tray in said vertical stack;
         said air gap of said each fermenting tray except for said top fermenting tray is greater than or equal to 5 cm and less than or equal to 12 cm;
         said each fermenting tray further comprises a drainage spout coupled to the bottom of said each fermenting tray;
         said bottom of said each fermenting tray is sloped such that an opening of said drainage spout is at a lowest point in said bottom; and,
         said each fermenting tray is thermally conductive and is configured to provide heat to another fermenting tray in said vertical stack, wherein said fermentation process occurs without an external source of heating of said ten or more fermenting trays.

* * * * *